US008057489B2

(12) United States Patent
Stone et al.

(10) Patent No.: US 8,057,489 B2
(45) Date of Patent: Nov. 15, 2011

(54) METHOD AND APPARATUS FOR PASSING A SUTURE

(75) Inventors: Kevin T. Stone, Winona Lake, IN (US); Troy M. Walters, Plymouth, IN (US); Ryan A. Kaiser, Leesburg, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 172 days.

(21) Appl. No.: 12/539,299

(22) Filed: Aug. 11, 2009

(65) Prior Publication Data

US 2009/0306684 A1 Dec. 10, 2009

Related U.S. Application Data

(62) Division of application No. 11/386,074, filed on Mar. 21, 2006, now Pat. No. 7,572,265.

(51) Int. Cl.
*A61B 17/10* (2006.01)
*A61B 17/04* (2006.01)
*A61B 17/00* (2006.01)

(52) U.S. Cl. ......... 606/139; 606/144; 606/148; 606/205

(58) Field of Classification Search .................. 606/139, 606/144, 145, 148, 205, 216
See application file for complete search history.

(56) References Cited

U.S. PATENT DOCUMENTS 3,349,772 A 10/1967 Rygg
3,842,840 A 10/1974 Schweizer
3,946,740 A 3/1976 Bassett
3,946,840 A 3/1976 Sommer
4,164,225 A 8/1979 Johnson et al.
4,890,615 A 1/1990 Caspari et al.
4,923,461 A 5/1990 Caspari et al.
4,957,498 A 9/1990 Caspari et al.
5,163,945 A 11/1992 Ortiz et al.
5,188,636 A 2/1993 Fedotov
5,192,287 A 3/1993 Fournier et al.
5,222,962 A 6/1993 Burkhart
5,224,948 A 7/1993 Abe et al.
5,242,458 A 9/1993 Bendel et al.
5,254,126 A 10/1993 Filipi et al.
5,257,637 A 11/1993 El Gazayerli
(Continued)

FOREIGN PATENT DOCUMENTS

DE 4235602 A1 4/1994
(Continued)

OTHER PUBLICATIONS

ExpresSew™. Surgical Solutions. (2003) http://www.surgicalsolutions.com/products/index.html Web. Jul. 30, 2004 (2 sheets).

(Continued)

*Primary Examiner* — S. Thomas Hughes
*Assistant Examiner* — Melissa Ryckman
(74) *Attorney, Agent, or Firm* — Harness, Dickey

(57) ABSTRACT

A suture pushing device includes a handle, a shaft extending from the handle, and a suturing head at the distal end of the shaft. The suturing head includes a first jaw and a second jaw. The first jaw and/or the second jaw have a tissue cutting edge adapted to cut an opening in a tissue. A blunt suture pushing member advances from within the shaft, through the suturing head, and through the cut opening in the tissue to place a suture.

20 Claims, 10 Drawing Sheets

U.S. PATENT DOCUMENTS 5,312,423 A 5/1994 Rosenbluth et al.
5,318,577 A 6/1994 Li
5,318,579 A 6/1994 Chow
5,382,258 A 1/1995 Chow
5,397,325 A 3/1995 Della Badia et al.
5,405,351 A 4/1995 Kinet et al.
5,417,701 A 5/1995 Holmes
5,454,823 A 10/1995 Richardson et al.
5,474,565 A 12/1995 Trott
5,478,345 A 12/1995 Stone et al.
5,501,692 A 3/1996 Riza
5,522,820 A 6/1996 Caspari et al.
5,545,170 A 8/1996 Hart
5,562,683 A 10/1996 Chan
5,575,801 A 11/1996 Habermeyer et al.
5,601,573 A 2/1997 Fogelberg et al.
5,618,290 A 4/1997 Toy et al.
5,653,716 A 8/1997 Malo et al.
5,702,407 A 12/1997 Kaji
5,713,908 A 2/1998 Jameel et al.
5,730,747 A 3/1998 Ek et al.
5,772,672 A 6/1998 Toy et al.
5,776,150 A 7/1998 Nolan et al.
5,820,628 A 10/1998 Middleman et al.
5,824,009 A 10/1998 Fukuda et al.
5,868,760 A 2/1999 McGuckin, Jr.
5,895,393 A 4/1999 Pagedas
5,921,993 A 7/1999 Yoon
5,935,138 A 8/1999 McJames, II et al.
5,935,149 A 8/1999 Ek
5,947,982 A 9/1999 Duran
5,957,936 A 9/1999 Yoon et al.
6,051,006 A 4/2000 Shluzas et al.
6,077,277 A 6/2000 Mollenauer et al.
6,171,316 B1 1/2001 Kovac et al.
6,533,795 B1 3/2003 Tran et al.
6,626,929 B1 9/2003 Bannerman
6,638,283 B2 * 10/2003 Thal .............................. 606/144
6,648,902 B2 11/2003 Colgan et al.
6,663,641 B1 12/2003 Kovac et al.
6,723,107 B1 4/2004 Skiba et al.
6,743,241 B2 6/2004 Kerr
6,770,084 B1 8/2004 Bain et al.
6,896,686 B2 5/2005 Weber
6,984,237 B2 1/2006 Hatch et al.
7,082,337 B2 * 7/2006 Sommer et al. ............... 607/132
7,112,208 B2 9/2006 Morris et al.
7,377,926 B2 5/2008 Topper et al.
7,381,212 B2 6/2008 Topper et al.
7,879,046 B2 2/2011 Weinert et al.
2001/0012945 A1 8/2001 Romano
2001/0016747 A1 8/2001 Romano et al.
2002/0147456 A1 10/2002 Diduch et al.
2002/0169455 A1 11/2002 Bannerman et al.
2003/0065337 A1 4/2003 Topper et al.
2003/0208187 A1 11/2003 Layer
2003/0208207 A1 11/2003 Layer
2003/0233106 A1 12/2003 Dreyfuss
2004/0176802 A1 9/2004 Skiba et al.
2004/0199184 A1 * 10/2004 Topper et al. ................. 606/144
2004/0249394 A1 12/2004 Morris et al.
2004/0260314 A1 12/2004 Lizardi et al.
2005/0234479 A1 10/2005 Hatch et al.
2005/0288690 A1 12/2005 Bourque et al.
2006/0020273 A1 1/2006 Hatch et al.
2007/0060953 A1 3/2007 Morris et al.
2007/0149986 A1 6/2007 Morris et al.
2007/0225735 A1 9/2007 Stone et al.
2009/0306684 A1 12/2009 Stone et al.

FOREIGN PATENT DOCUMENTS

EP 0778004 A1 6/1997
WO WO-9843545 A1 10/1998

OTHER PUBLICATIONS

Introducing ExpresSewn™. Surgical Solutions. http://www.surgicalsolutions.com Web. Jul. 30, 2004 (1 sheet).

The ExpresSew™ Suture Passer, The First “One Pass, One Portal” Suture Passer Under 5mm, brochure. Surgical Solutions™ (2002) 2 sheets.

* cited by examiner

FIG. 5A
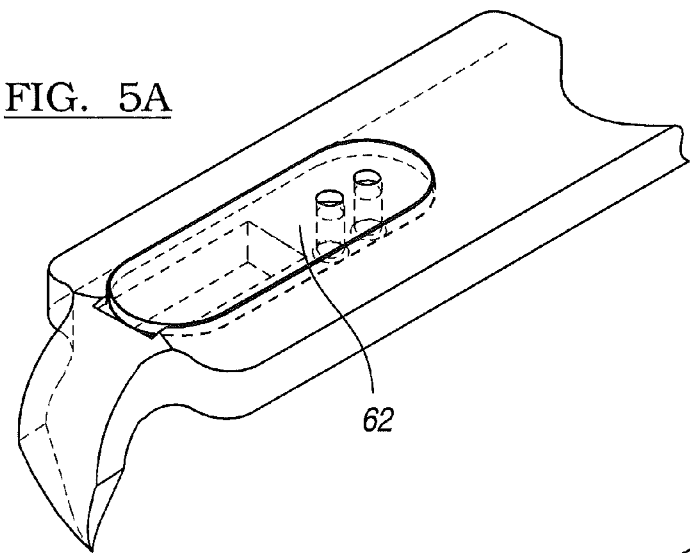
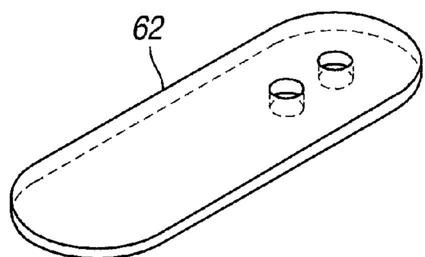
FIG. 5B
FIG. 6A
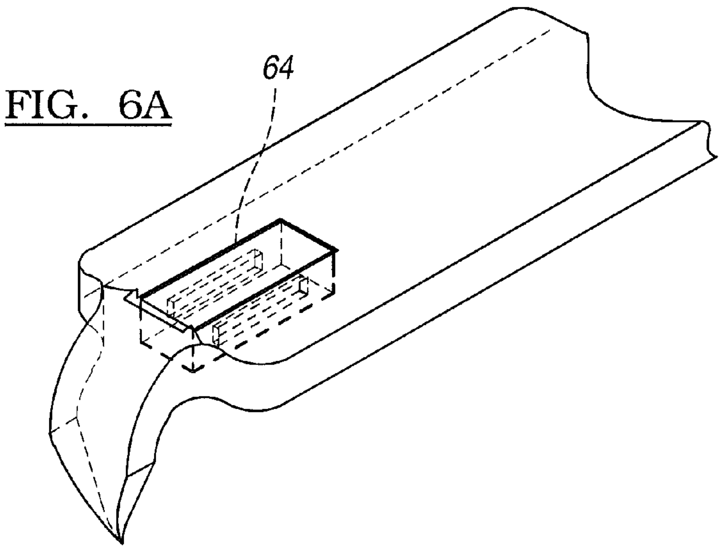
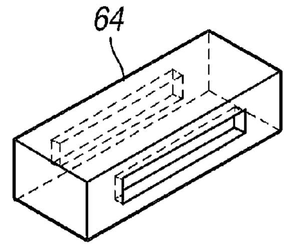
FIG. 6B

METHOD AND APPARATUS FOR PASSING A SUTURE

CROSS-REFERENCE TO RELATED APPLICATIONS

This application is a divisional application of U.S. patent application Ser. No. 11/386,074, filed on Mar. 21, 2006, now U.S. Pat. No. 7,572,265. The entire disclosure of the above application is incorporated herein by reference in its entirety.

FIELD

The present disclosure relates to methods and apparatus for passing a suture through tissue.

BACKGROUND

Various devices and methods are known for suturing soft tissue in connection with arthroscopic, endoscopic, or other surgical procedures. These and other small-incision or less invasive surgical procedures require that suturing and the associated manipulation of suturing needles are performed in confined areas which are not easily accessible.

Although the existing devices can be satisfactory for their intended purposes, there is still a need for procedures and devices that provide greater control in the passage of sutures, greater control in the passage of delicate sutures, and increased flexibility in the types and thicknesses of tissues which can be sutured in ordinary and in less invasive procedures.

SUMMARY

The present teachings provide a suture pushing device comprising a handle, a shaft extending from the handle, and a suturing head at the distal end of the shaft. The suturing head includes a first jaw and a second jaw. At least one of the first jaw or the second jaw has a tissue cutting edge adapted to cut an opening in a tissue. The second jaw is coupled to the first jaw. A blunt suture pushing member advances from within the shaft, through the suturing head, and through the cut opening in the tissue. The device can further include a suture where the suture is carried by the blunt suture pushing member through the cut opening in the tissue. The suture pushing device can optionally include a suture delivery channel to hold the suture, a suture pushing member receptacle to receive the blunt suture pushing member, or a suture retention mechanism to maintain the suture at the suturing head.

The blunt suture pushing member can contain a plurality of roughened surface features on the distal end of the blunt suture pushing member. The roughened surface features are non-piercing surface features. The blunt suture pushing member can be made of a flexible material, for example, a Nitinol wire.

The suture pushing device handle can include a trigger and a hammer. The trigger is actuable to move the second jaw and the first jaw in relation to each other. The hammer is actuable to advance the blunt suture pushing member through the cut opening in the tissue. The suture pushing device can include a ramp for advancement of the flexible blunt suture pushing member. The ramp can be in communication with the suture pushing member receptacle. The suture pushing device can also include a suture delivery channel.

The present teachings also provide methods for pushing suture through a tissue. A tissue is captured between a pair of jaws. The tissue is pierced by at least one of the jaws to form an opening in the tissue. The suture is carried through the opening. The suture can be loaded in one of the jaws. The suture can be carried through the opening by moving a pusher member adjacent to the suture from a retracted position to an advanced position. The suture can be held in one of the jaws. The tissue opening can be of a sufficient diameter to allow clearance of the blunt suture pushing member through the opening without requiring piercing of the tissue by the blunt suture pushing member. The opening can be maintained by hand compression of a trigger that is operable to facilitate cutting the tissue with the jaw.

The present teachings also provide a method for pushing suture through a tissue. A pre-formed hole is formed in the tissue. The suture is pushed through the pre-formed hole with a blunt suture pushing member that advances through the pre-formed hole.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIGS. 5A and 5B depict a suture retaining mechanism according to the present teachings;

FIGS. 6A and 6B depict a suture retaining mechanism according to the present teachings;

DETAILED DESCRIPTION

Figure 1:
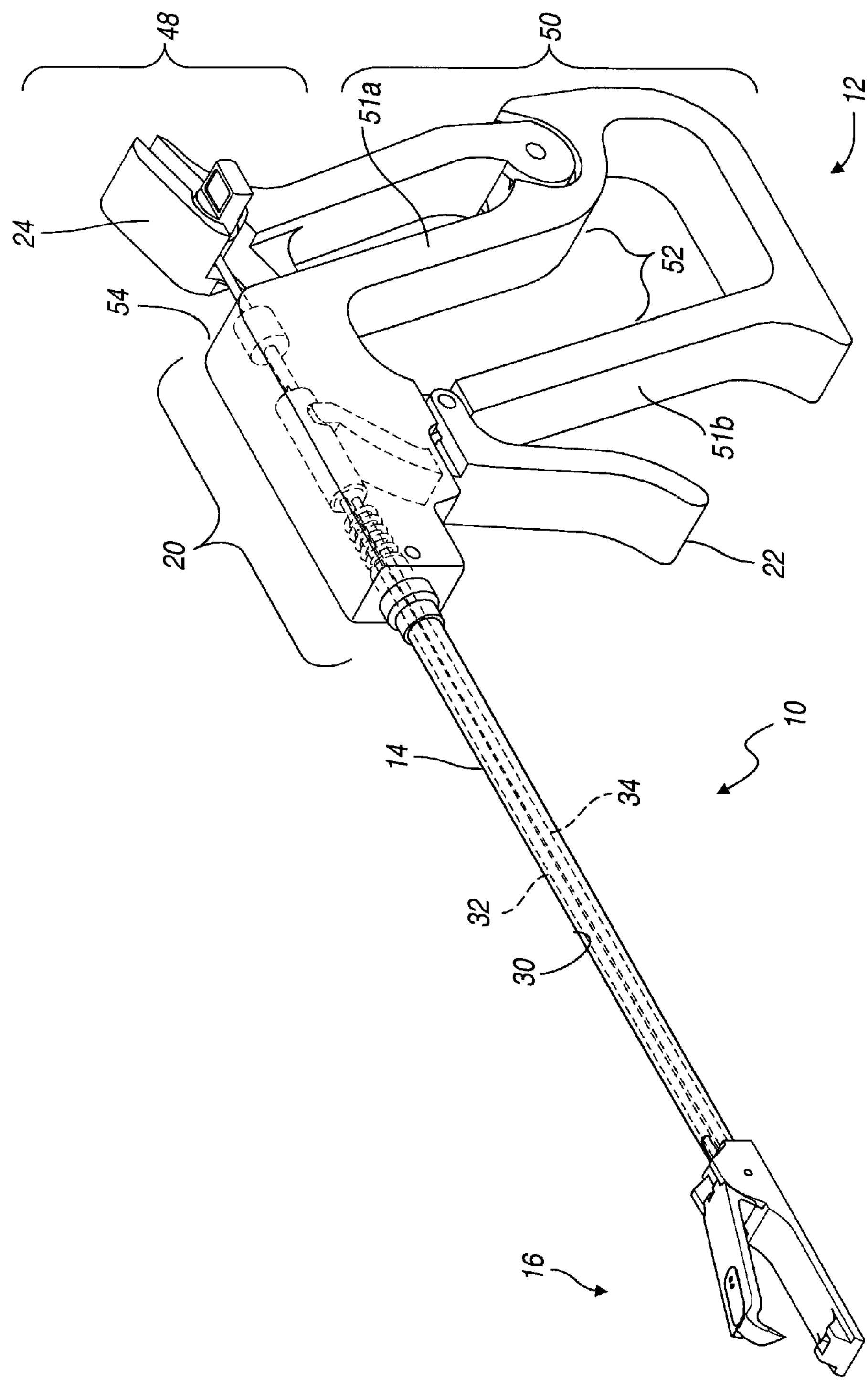
FIG. 1 depicts an isometric view of an embodiment of a suture pushing device according to the present teachings.

The following description is merely exemplary in nature and is not intended to limit the present disclosure, application, or uses.

Referring to FIGS. 1, 2A, 2B, 3A, 3B, and 4, a suture pushing device 10 is provided. Unless specifically mentioned, the various components of the suture pushing device 10 are made of a biocompatible compatible material, such as stainless steel to allow for sterilization using chemicals or autoclaving. It is understood that select components pointed out herein can be made from non-stainless steel materials and therefore those select components may not be suitable for all sterilization techniques due to heat sensitivity or chemical sensitivity of the materials. Moreover, select components may also be single-use or disposable components that are replaced after each procedure.

The suture pushing device 10 comprises a handle 12, a shaft 14, a suturing head 16, and a blunt suture pushing member 18. The handle 12 includes a handle body 20, a trigger 22, and a hammer 24. The handle body 20 contains a trigger spring 26 connected to and actuated by the trigger 22. The handle body 20 contains a hammer spring 28 connected to and actuated by the hammer 24. The shaft 14 defines a channel 30 housing a trigger arm 32 and a hammer actuation path 34. The channel 30 trigger arm 32 carries the trigger spring force through the shaft 14. The channel 30 hammer actuation path 34 receives the hammer spring force to deliver the suture pushing member 18.

The suturing head 16 and the blunt suture pushing member 18 are located at the distal end of the channel 30. The suturing head 16 includes a first jaw 36 and a second jaw 38. The first jaw 36 and the second jaw 38 are pivotally coupled together at a pivot point 40 over pin 42 such that at least one of the first jaw 36 or the second jaw 38 pivots with respect to the other jaw. The trigger 22 action is translated through the trigger spring 26 to the trigger arm 32 and to either or both of the jaws, such that either or both of the jaws pivot over pin 42. A jaw cutting edge 44 can be contained on either jaw or on both jaws to cut an opening into and through the tissue.

The blunt suture pushing member 18 is contained within either of the first jaw 36 or the second jaw 38. Actuation of the hammer 24 causes the blunt suture pushing member 18 to advance up a ramp 46 contained in at least one of the first jaw 36 or the second jaw 38 and into the other jaw. The blunt suture pushing member 18 carries a suture 58 through the opening cut into the tissue.

The handle 12 is located at the proximal end of the suture pushing device 10. The handle 12 includes the handle body 20, the trigger 22, and the hammer 24. The handle body 20 includes an upper region 48, a lower region 50, and a central hollow region 52 as defined by the arms 51*a* and 51*b* which connect the upper region 48 to the lower region 50. The handle upper region 48 houses the trigger spring 26. The trigger spring 26 is connected to and actuated by the trigger 22. As depicted, trigger 22 can be a generic lever which can be depressed to engage the trigger spring 26. The hammer spring 28 is connected to and actuated by the hammer 24. The hammer spring 28 is located between the handle body 20 at arm 51*a* and the hammer 24. The hammer spring 28 as depicted is a simple, single spring, but it is understood that the hammer spring 28 can be a spring system having multiple springs. As depicted, the hammer 24 is also a generic lever which can be depressed to engage the hammer spring 28.

As depicted, the handle 12 is adapted to be grasped by the hand of an operator. The fingers of the operator would engage the trigger 22, the palm of the operator would engage a lower region of the handle body 20 and the thumb of the operator would engage the hammer 24. The handle body 20 as depicted is merely for convenience and it is understood that any suitable handle can be substituted for the handle 12 as disclosed herein. Moreover, minor variations, such as re-arranging the spatial order of the trigger 22 and the hammer 24 or enclosing the central hollow region 52, of the handle 12 as described herein are also within the scope of the present teachings.

The shaft 14 is located at the distal end of the handle 12. As depicted, the shaft 14 is substantially planar or aligned with the upper surface 54 of the handle 12. The shaft can also be angled respective to the upper surface 54 of the handle 12. The shaft 14 can be angled down, up, to the left, or to the right with respect to the upper surface 54 to any exemplary non-limiting angle, such as 45°, 90°, or 120°, for example. The shaft 14 can also be curved along the shaft 14 at the proximal end, distal end, or any point between. The curve may be directed to the right, left, up, or down. The shaft 14 while shown to be rigid, can also be flexible if desired.

The shaft 14 houses the trigger spring arm 32 and the hammer actuation path 34. The trigger spring arm 32 is connected to the trigger spring 26 in the handle body 20. The hammer actuation path 34 is connected to the hammer 24 in the handle body 20. As disclosed in greater detail later herein, actuation of the hammer 24 is translated into advancement of the suture pushing member 18 and actuation of the trigger 22 is translated into pivotal movement of the jaw or jaws about the pin 42.

Figure 2A:
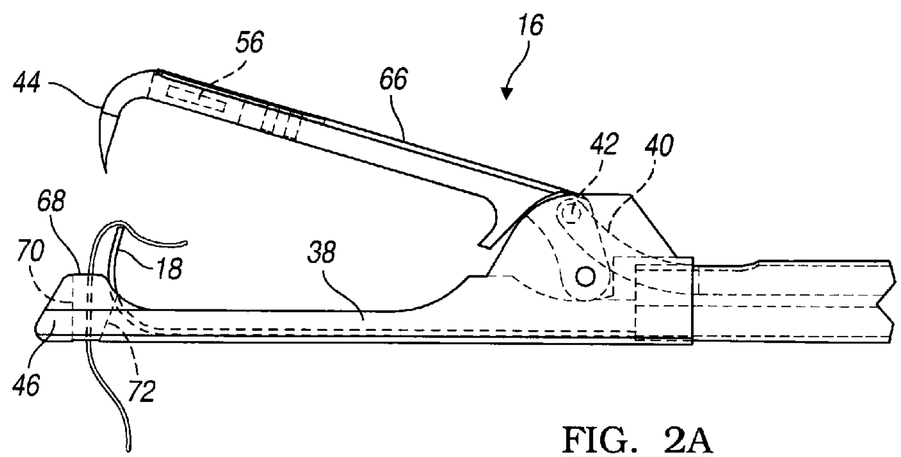
FIGS. 2A and 2B depict views of a suturing head in an open position according to the present teachings.
Figure 2B:
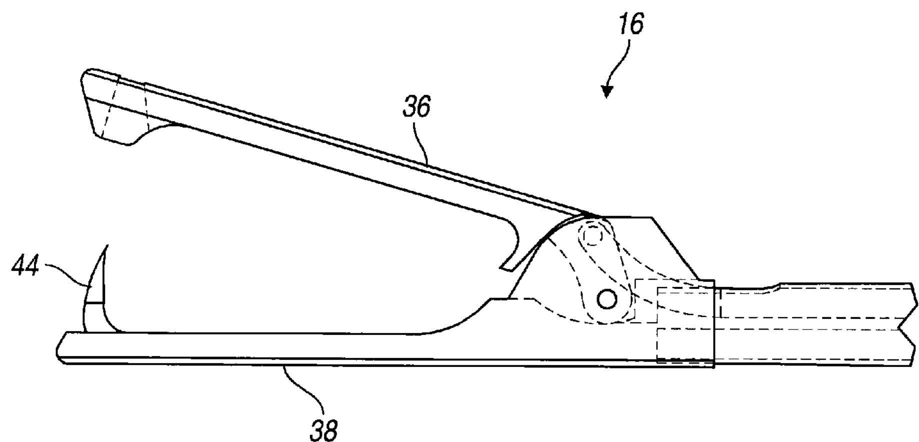
Figure 3A:
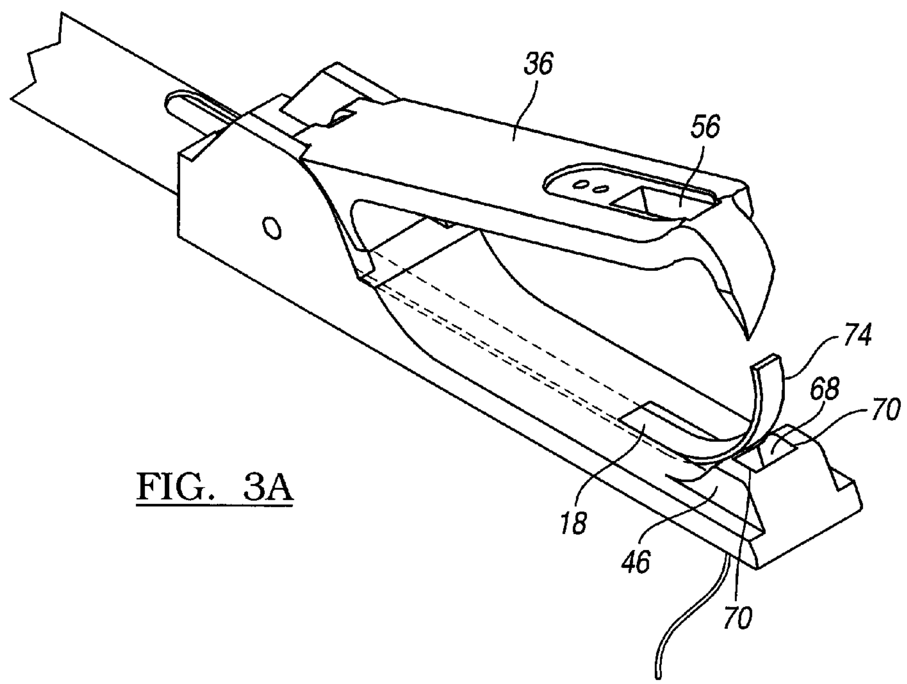
FIGS. 3A and 3B depict views of a suturing head in a closed position according to the present teachings.
Figure 3B:
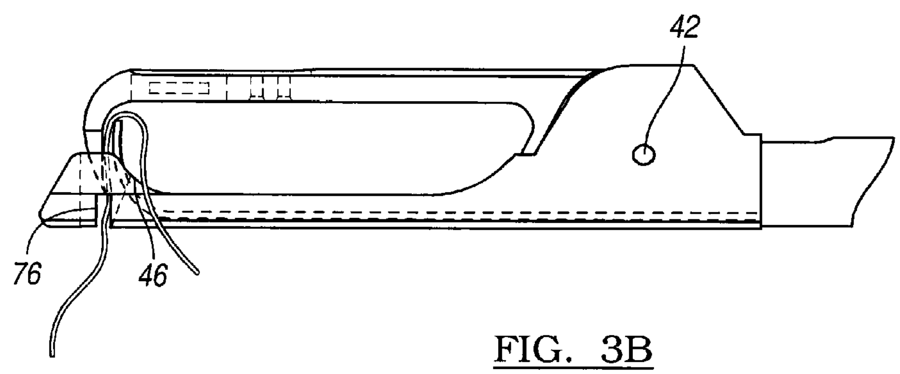
Figure 4:
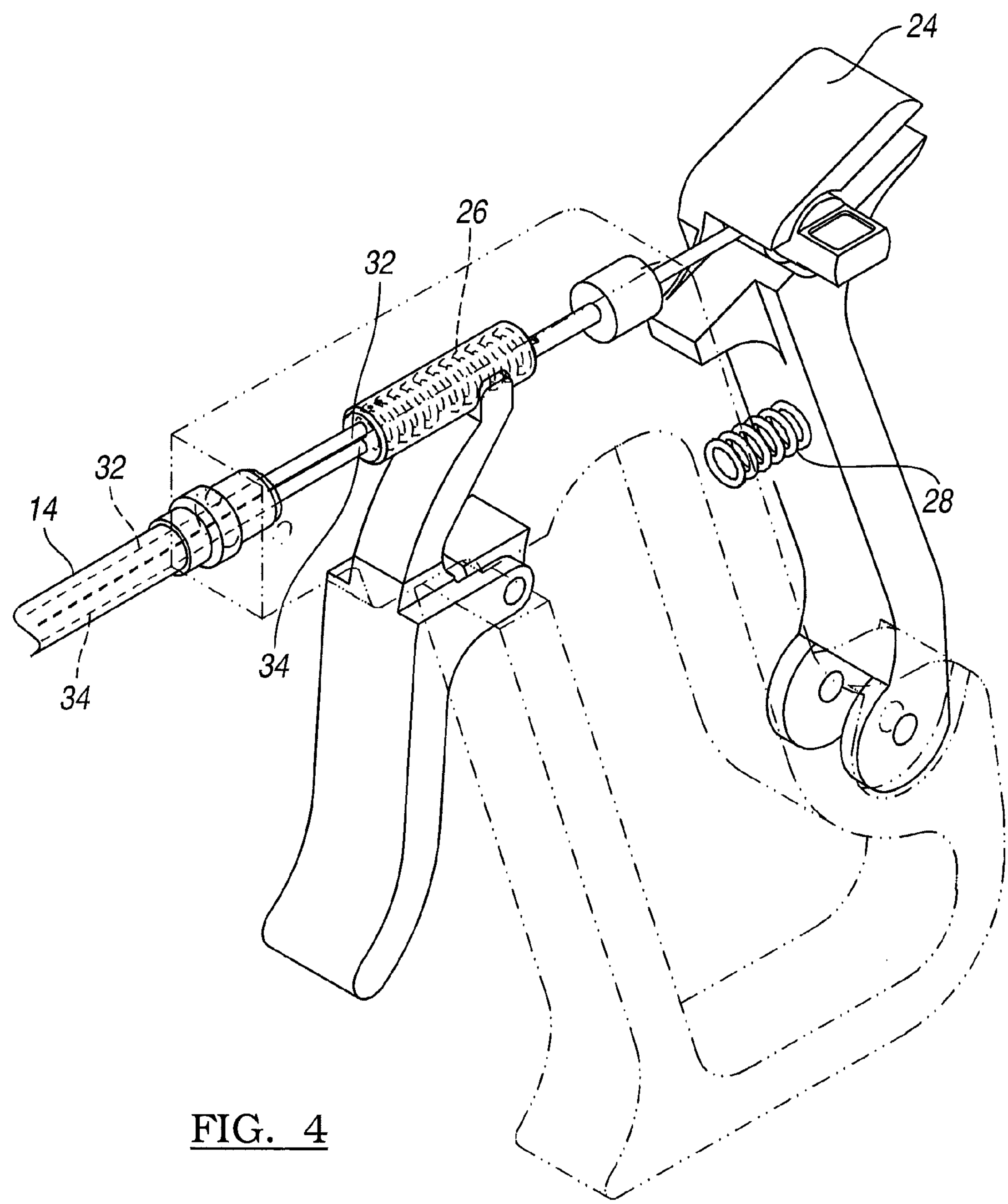
FIG. 4 depicts an opening in a first jaw according to the present teachings.

The suturing head 16 and the blunt suture pushing member 18 are located at the distal end of the shaft 14. The suturing head 16 includes a first jaw 36 and a second jaw 38. The first jaw 36 and the second jaw 38 are pivotally engaged with pin 42. Either or both of the jaws can pivot with respect to the other jaw about the pin 42. The jaw or jaws can move away from the other jaw, as shown in FIGS. 2A and 2B, to an the open position or the jaw or jaws can move towards each other into partially closed position or fully closed position, as shown in FIGS. 3A and 3B. At least one of the jaws moves toward the other jaw such that when the cutting edge 44 moves in closer proximity with the opposing jaw, the blunt suture member 18 aligns with and is received by the suture pushing member receptacle 56.

A tissue cutting edge 44 can be on either or both of the jaws. The tissue cutting edge 44 has a sharp point which is used to cut an opening into and through tissue. The knife or tooth-like nature of the tissue cutting edge 44 allows the suture pushing device 10 to be used with very thick tissue. In contrast, other suturing devices, which employ a needle that as a suture attached thereto to carry or push a suture through the tissue are limited to the strength of the needle and the force at which the needle pierces the tissue. By cutting the tissue with the tissue cutting edge 44, the suture pushing device 10 can be employed in less invasive operating techniques and is not limited by the particular thickness of the tissue being sutured. Although portions of the following description may illustrate the cutting edge 44 located on the first jaw 36 and items opposing the cutting edge (such as the blunt suture pushing member 18, the ramp 46, a suture delivery channel 76, etc.) being located on the second jaw 38, it is understood that in embodiments having a single cutting edge 44 located on the second jaw 38, the items opposing the cutting edge can be located in the first jaw 36.

In various embodiments, the first jaw 36 also includes a suture pushing member receptacle 56. As depicted in FIG. 3A, the suture pushing member receptacle 56 can be an opening in the first jaw 36. The suture pushing member receptacle 56 can be of any suitable size to accept the blunt suture pushing member 18 and a suture 58, as disclosed later herein.

Referring to FIGS. 5A, 5B, 6A, and 6B, the suture pushing member receptacle 56 can further include a suture retaining mechanism 60. The suture retaining mechanism 60 prevents the unintentional movement of a suture 58 out of the first jaw 36. The suture retaining mechanism 60 maintains the suture 58 at or near the suturing head 16. Referring to FIG. 5B, the suture retaining mechanism 60 can be a flexible flap 62 which fits over the suture pushing member receptacle 56. The flap 62 can be made of a resilient and flexible material, such as spring steel. The spring steel or other resilient material, such as a flexible polymer, allows for the blunt suture pushing member 18 to pass into the receptacle 56, temporarily disrupt the flap 62 from a closed position in full contact with the first jaw 36 to an open position with a space between the flap 62 and the first jaw 36, and retract through the flap 62 allowing the flap 62 to return to a closed position. In such an embodiment, the suture 58 would be partially held under the flap 62 of the suture retaining mechanism 60 and would partially extend beyond the flap and onto a first jaw upper surface 66.

As depicted in FIG. 6B, the suture retaining mechanism 60 can be a flexible block which can be temporarily dislodged from a closed position to an open position to facilitate passage of the blunt suture pushing member 18 into the receptacle 56. In such embodiments, the suture 58 would be held between the block 64 and the suture pushing member receptacle 56 and would partially extend beyond the block 64 and onto an upper surface of the first jaw 36. The block 64 can be made of a flexible silicone or other polymeric material which can be moved by the blunt suture pushing member 18, as described later herein.

In an embodiment where only one jaw contains a cutting edge 44, the jaw without the cutting edge 44 can include a tissue cutting edge receptacle 68 defined by sidewalls 70 to receive the tissue cutting edge 44. The tissue cutting edge 44 can be received on a pad 72 and can rest against or engage the side walls 70. The pad 72 is a generally flat surface which provides an at least partially continuous region to stop advancement of the tissue cutting edge 44 beyond the lower most surface of the jaw without the cutting edge 44. The pad 72 is a non-piercing or non-cutting surface.

The second jaw 38 is in communication with the hammer actuation path 34 to define a continuous channel 30 for the advancement of the blunt suture pushing member 18. As stated above herein, actuating the hammer 24 advances the blunt suture pushing member 18 along the second jaw 38.

The second jaw 38 can also include a ramp 46 or other inclined surface on which to orient the blunt suture pushing member 18 with the suture pushing member receptacle 56. The ramp 46 is oriented such that the blunt suture pushing member 18 extends towards the first jaw 36 and is aligned with the suture pushing member receptacle 56 in the first jaw. The ramp 46 and the suture pushing member receptacle 56 roughly provide reverse J-shaped path for the blunt suture pushing member 18 to follow. The blunt suture pushing member 18 follows the ramp 46 and curves upwards towards the suture pushing member receptacle 56 to guide the blunt suture pushing member 18 in a straight and non-curved direction through the opening in the first jaw 36.

The second jaw 38 can include the suture delivery channel 76 to receive and guide the suture 58. The suture delivery channel 76 can be a slot, a notch, a slit, or a hook shaped member to provide a region where the suture 58 can be placed for alignment with and subsequent carrying or pushing by the blunt suture pushing member 18. The suture delivery channel 76 is adapted to receive a "free" suture or a suture which is not attached to a needle or contained within a suture dispensing device, such as a spool. It may be advantageous to align the suture delivery channel 76 towards the center of the second jaw 38 such that upon advancing the blunt suture pushing member 18, the blunt suture pushing member 18 can amply hold or carry the suture 58.

The first jaw 36 and the second jaw 38 are moved with respect to each other by actuating the trigger 22 on the handle 12 to engage the trigger spring 26 and the trigger arm 32. Squeezing the trigger 22 causes a temporary position change of the first jaw 36 and/or the second jaw 38. A selected position between the first jaw 36 and the second jaw 38 can be maintained by keeping a constant manual pressure on the trigger 22 as the trigger 22 cannot be locked into a particular position. When the trigger is actuated or depressed, the moving jaw or jaws move in closer proximity to the other jaw. When depression of the trigger is lessened or is removed, the moving jaw or jaws move away from the other jaw thereby creating more distance between the first jaw 36 and the second jaw 38. When pressure is fully removed from the trigger 22, the jaws return to the resting position or the open position.

The second jaw 38 provides the substrate on which the blunt suture pushing member 18 advances from a retracted position to an advanced position. The blunt suture pushing member 18 can be made of a flexible material. Exemplary suitable materials include Nitinol or a flexible polymeric material.

The blunt suture pushing member 18 is generally flat and adapted to have a low or recessed profile within the second jaw 38. The blunt suture pushing member 18 is sized to fit with the second jaw 38 or to rest on top of the second jaw 38 without being caught by the cutting edge 44 or the pad 72. The blunt suture pushing member 18 can be disposable and the blunt suture pushing member 18 can be reloaded into the device as needed. The blunt suture pushing member 18 can be reloaded via the hammer 24 or the blunt suture pushing member 18 can be reloaded via the second jaw 38.

Figure 7A:
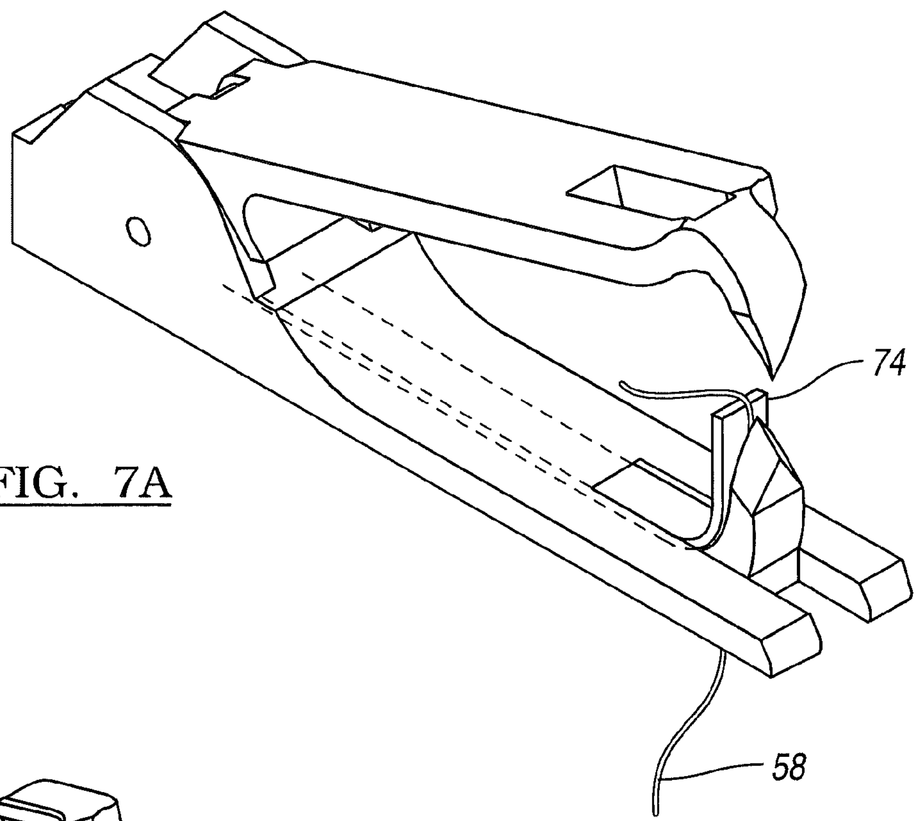
FIGS. 7A and 7B depict a blunt suture pushing member according to the present teachings.
Figure 7B:
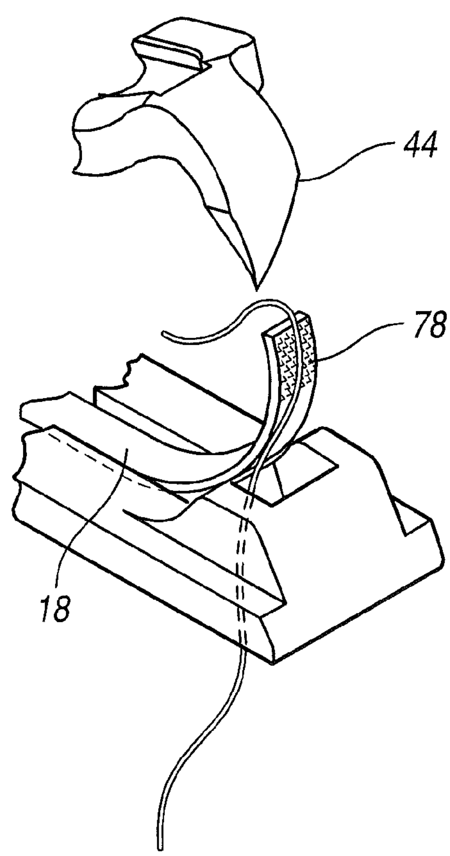
Figure 8:
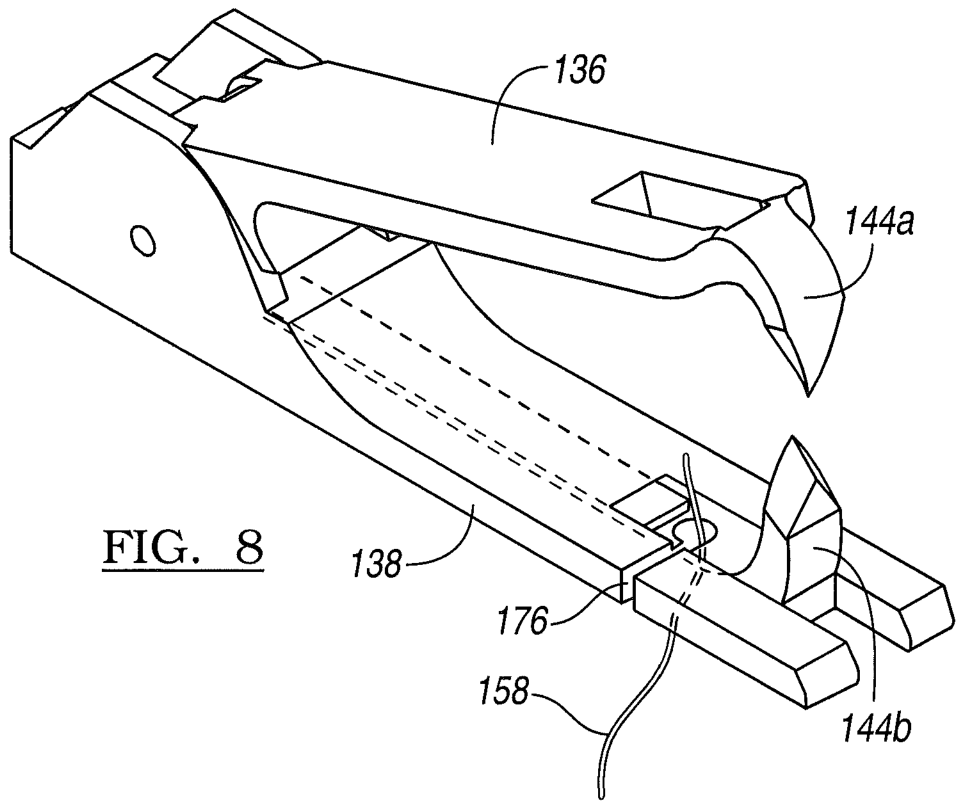
FIG. 8 depicts a suturing head having two cutting edges according to the present teachings.
Figure 9:
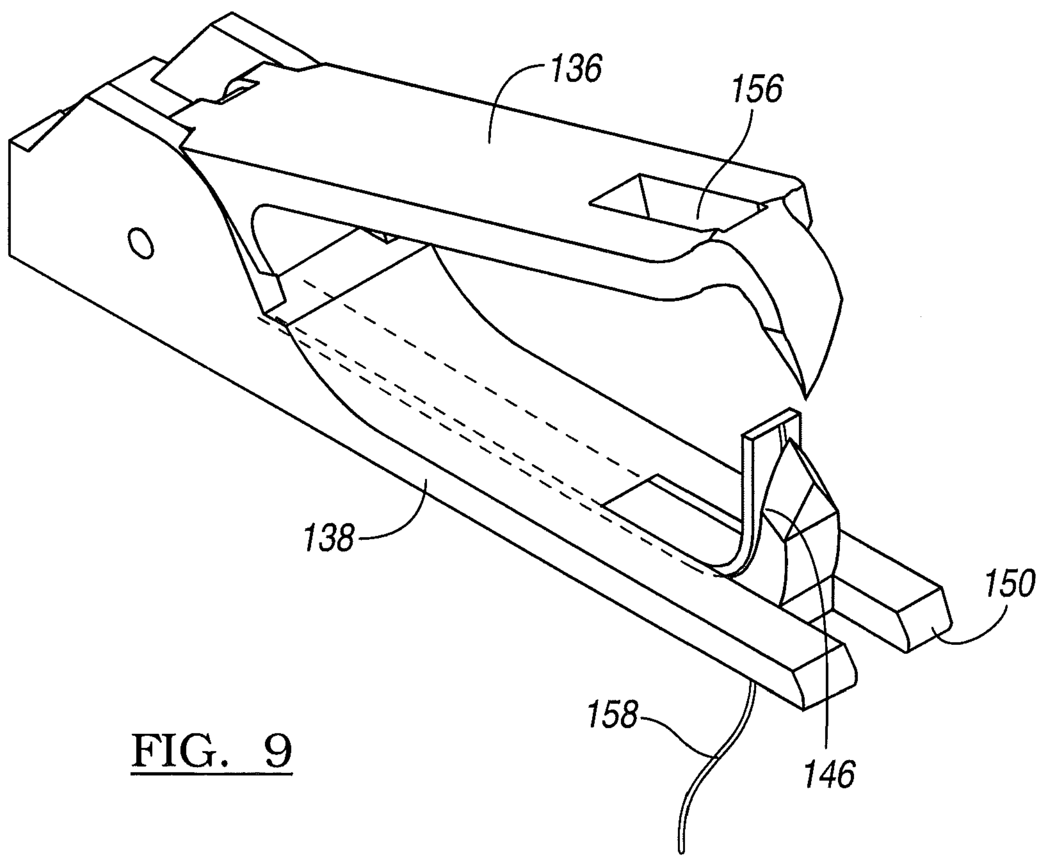
FIG. 9 depicts a suturing head heaving two cutting edges with the suture pushing in a partially deployed position according to the present teachings.
Figure 10:
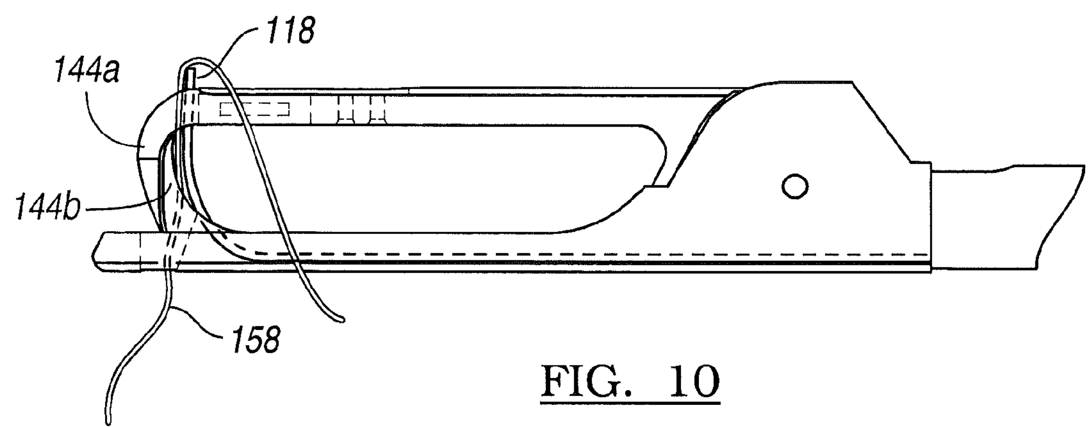
FIG. 10 depicts a suturing head where the two cutting edges are cross engaged and the suture pushing is in the partially deployed position according to the present teachings.

Referring to FIGS. 7A and 7B, the blunt suture pushing member 18 has a squared or blunt end 74 which is free from any sharp, pointed, or piercing features. The blunt end 74 can be substantially smooth or can have a rounded end. The blunt suture pushing member has a generally rectangular end and cross-section. The generally rectangular end can have slight rounding at the distal most tip of the blunt suture pushing member 18. The blunt suture pushing member 18 engages the suture 58 from the suture delivery channel 76 and advances the suture 58 from the second jaw 38 to the suture pushing member receptacle 56.

The blunt or smooth characteristic of the blunt suture pushing member 18 allows for greater flexibility in the types of suture 58 which can be used with the suture pushing device 10. For example, the blunt suture pushing member 18 used in conjunction with the pre-cut opening in the tissue made by the cutting edge 44 allow for a delicate suture or a very fine gauge suture to be employed without concerns of damage to the suture which would normally accompany the use of a needle having a rigid and set opening through which to advance the suture that is attached to the needle. In the needled system having a rigid and set opening, stress is placed on the suture as is spans across opposing sides of the eyelet. The stress on the suture in addition to being compressed when the needle carrying the suture pierces the intact tissue to form a hole, damages the suture and increases the stress on the suture across the eyelet. In contrast to a needled system, the suture pushing device 10 according to various embodiments of the present teachings does not place intense and focused load stress on the suture due to an eyelet in a needle being pushed through a tissue while simultaneously piercing the tissue.

In various embodiments, the blunt suture pushing member 18 can contain a plurality of roughened surface features 78 on the blunt end 74. The roughened surface features 78 are non-piercing surface features, including, but not limited to microabrasions. The roughened surface features 78 do not significantly alter the shape of the blunt suture pushing member 18 end The roughened surface features 78 can also include a coating of a textured material on the blunt suture pushing member 18.

The blunt suture pushing member 18 can be moved from a non-deployed or retracted position which is closer to the handle to a deployed position which is closer to the suturing head by actuating the hammer 24. The hammer is connected to the blunt suture pushing member 18 with a spring. Depressing the hammer 24, for example with a thumb of an operator, advances the blunt suture pushing member 18. When the thumb of the operator is removed from the hammer 24, the blunt suture pushing member 18 returns to a non-deployed state.

The description, interconnection of the components, and passage of the suture 58 as detailed above are also applicable to embodiments where the suture pushing device includes tissue cutting edges on both jaws. Referring to FIGS. 8 through 10 and 11, in various embodiments, the suture pushing device includes a suturing head 116 having a first actuable jaw 136 having a tissue cutting edge 144*a* and a second actuable jaw 138 coupled to the first jaw 136, the second jaw 138 having a tissue cutting edge 144*b*. Upon actuating the first jaw 136 and the second jaw 138, the first jaw tissue cutting edge 144*a* and the second jaw tissue cutting edge 144*b* engage to cut an opening into and through tissue. The device further includes a blunt suture pushing member 118 which advances from within the shaft 114, through the suturing head 116, and through the cut opening in the tissue.

Figure 11:
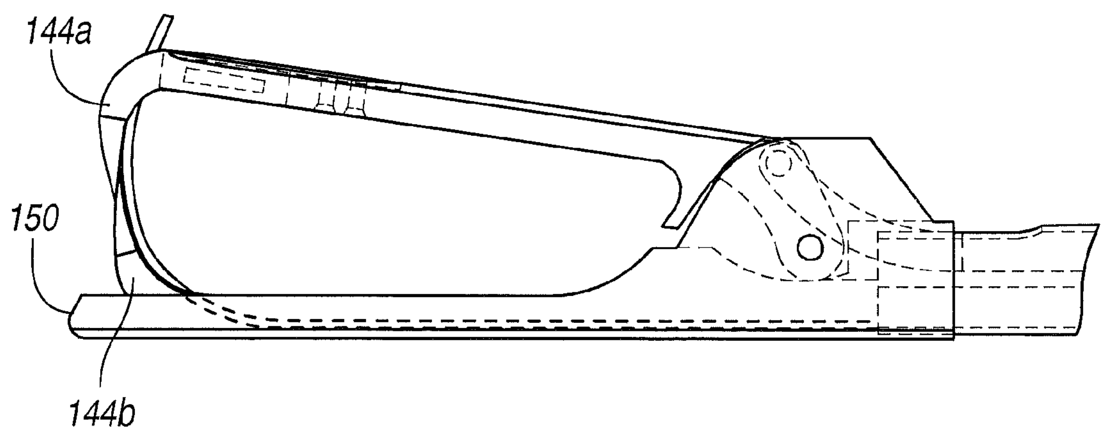
FIG. 11 depicts a side view of the two cutting edges partially closed and the suture pushing in the deployed position according to the present teachings.

The jaws 136, 138 can be in alignment and when actuated, the jaws 136 and 138 will follow along the same arcuate path towards each other. When the first jaw 136 and the second jaw 138 cross, the first jaw cutting edge 144*a* and the second jaw cutting edge 144*b* will cut an opening into the tissue. The device can also include a stop 150 located on either jaw to prevent the jaws from passing each other. The stop 150, as depicted in FIG. 11, can be a rectangular protrusion used to limit the passage of the second jaw cutting edge 144*b* into the suture pushing receiving receptacle 156 in the first jaw 136. The suture pushing receiving receptacle 156 in the first jaw is in communication with the cut tissue opening. The passage in the tissue formed by the cutting edges facilitates passage of the blunt suture pushing member 118 and the suture 158 carried therewith through the opening in the tissue without damaging or placing stresses on the suture 158. The actuation of the jaws and the blunt suture pushing member 118 and the materials and various subcomponents thereof are the same as those disclosed in embodiments having only a single cutting edge 144.

Figure 12A:
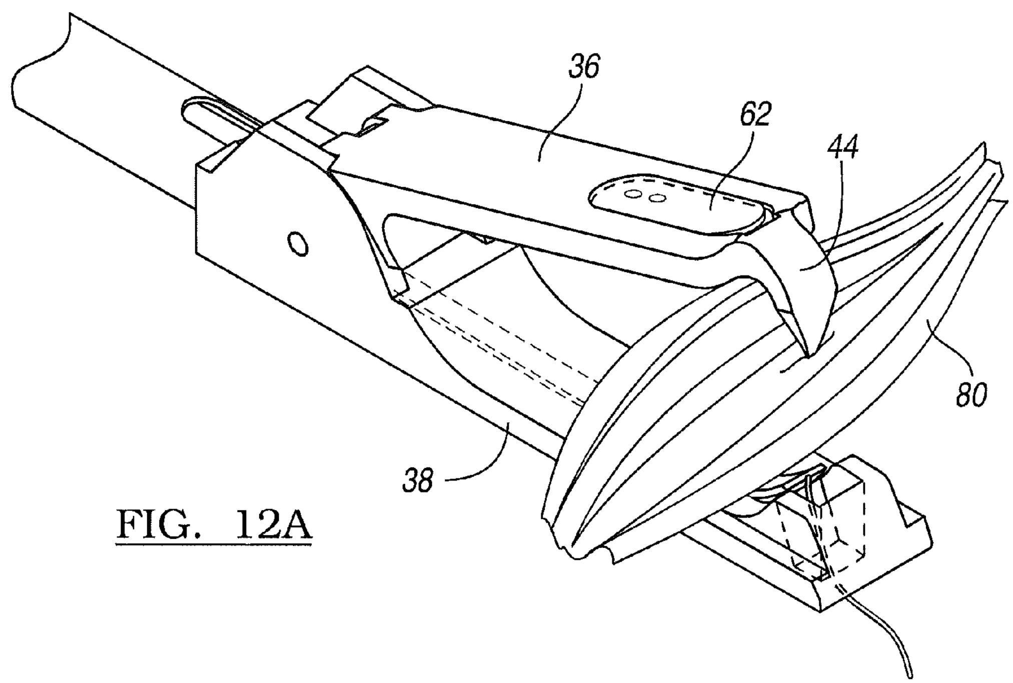
FIGS. 12A through 12C depict a surgical method according to the present teachings.
Figure 12B:
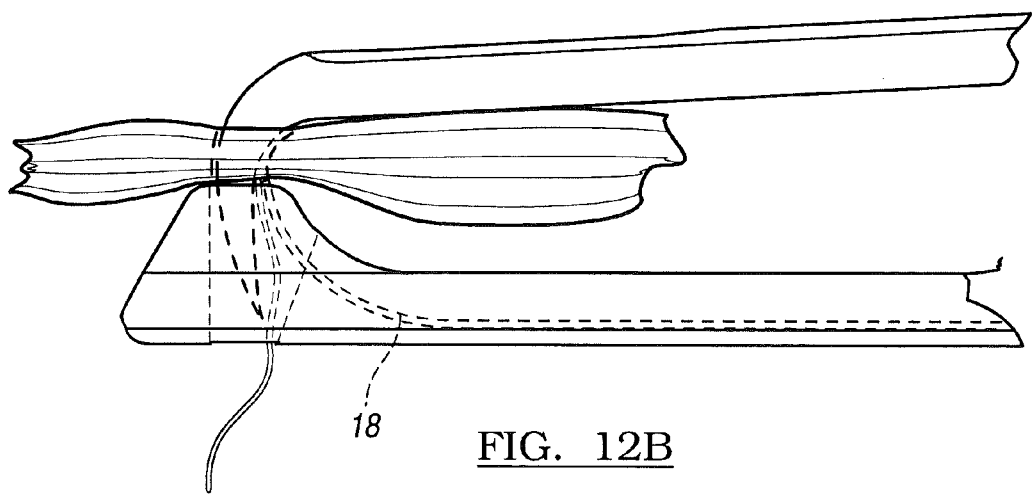
Figure 12C:
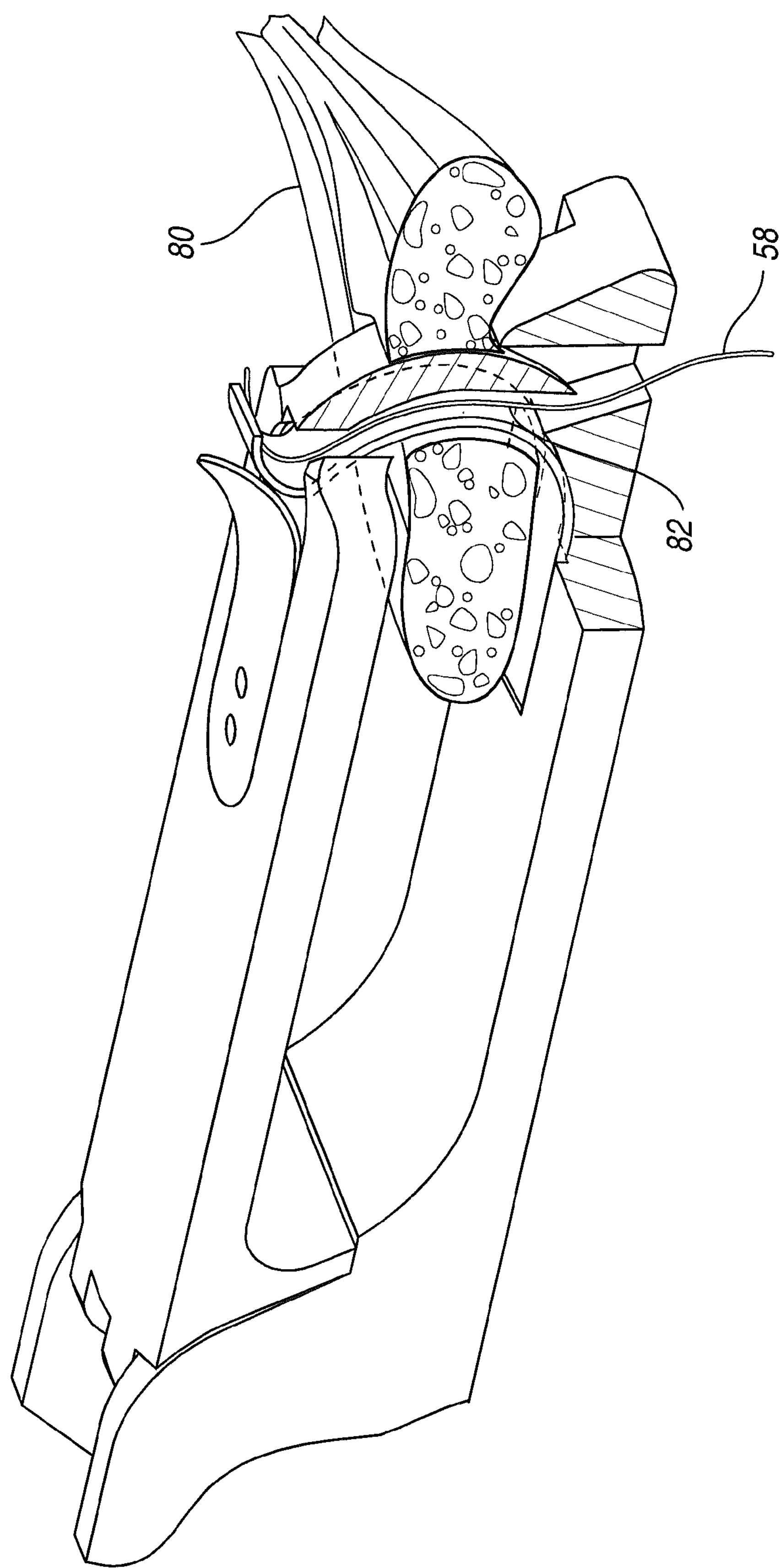

Referring to FIGS. 12A to 12C, the present teachings also provide methods for suturing a tissue and methods for pushing suture through a pre-formed opening in tissue. Although the methods are depicted and disclosed in conjunction with the embodiment having the suture pushing device including a first jaw 36 with a cutting edge 44 and a second jaw 38 having a pad formed thereon, it is understood that the general method is applicable to any of the embodiments disclosed herein.

An operator arranges suture 58 for engagement with the blunt suture pushing member 18. The suture 58 is placed into suture delivery channel 76 which is aligned with the blunt suture pushing member 18. The operator grasps the device 10 at the handle 12. A thumb of the operator can be placed on the hammer 24 while one or several of the opposing fingers can be wrapped around the trigger 22. The operator places the suture pushing device 10 in close proximity to the tissue 80 in need of suturing. The operator squeezes the trigger to create a tissue engaging opening 82 between the first jaw 36 and the second jaw 38. The handle 12 can be rotated to further align the first jaw 36 and the second jaw 38 with respect to the tissue 80, if needed.

To prepare the opening 82 in the tissue 80, the operator releases pressure on the trigger 22 to cause the first jaw 36 and the second jaw 38 to move in closer proximity with each other. When the first jaw cutting edge 44 depresses on the tissue 80, the cutting tip engages the tissue 80 and causes the opening 82 to be created therein. In embodiments, such as those described above where the suture pushing device 10 includes a pad 72 on the second jaw 38, the pad 72 will stop the advancement of the first jaw cutting edge 44. The pad 72 also keeps the first jaw cutting edge 44 in the tissue to keep the opening cut in the tissue in an expanded state as depicted. The first jaw cutting edge 44 releasably engages the pad 72 as the pad and the first jaw cutting edge 44 are only kept in contact so long as the trigger 22 is depressed. The expanded state of the opening collapses around the suture when the cutting edge 44 is advanced away from the opening 82.

The operator depresses the hammer 24 to advance the blunt suture pushing member 18. The hammer 24 actuates the spring 28 which in turn causes the blunt suture pushing member 18 to advance distally towards the suturing head 16. The ramp 46 is used to guide the blunt suture pushing member 18. When the hammer 24 is partially actuated, the blunt suture pushing member 18 obtains the suture 58 along the blunt end 74. When the hammer 24 is fully actuated or depressed, the blunt suture pushing member end 74 loosely carries the suture 58 then advances and the blunt suture pushing member 18 and the suture 58 through the pre-formed tissue opening 82. The blunt suture pushing member 18 displaces the flap 62 to advance the suture through the first jaw 36. The opening 82 in the tissue is of a sufficient diameter to facilitate clearance of the blunt suture pushing member 18 without requiring the pusher to pierce the tissue.

The operator then ceases and withdraws depression of the hammer which causes the blunt suture pushing member 18 to retract towards the shaft 14. As shown in FIG. 12C, when the blunt suture pushing member 18 retracts towards the shaft, the suture 58 is held in the opening 82. The operator then releases the trigger 22 to cause the first jaw 36 and the second jaw 38 to separate and return to the open position. When the cutting edge 44 in the first jaw 36 is removed from the tissue, the tissue "collapses" or the opening which was held by the cutting surface is no longer in the expanded position and comes within a closer proximity to the suture 58.

The operator can continue to suture the tissue at nearby regions or at other regions by moving the suture pushing device 10 and repeating the process of cutting the tissue with the cutting edge 44 and advancing the blunt suture pushing member 18 carrying or pushing the suture 58 through that opening in the tissue. After the suture is placed in the tissue, the suture 58 can be knotted using any suitable means. The suture 58 can also be manipulated using other tools such as a suture retriever or a suture grasper.

Suitable procedures can include, but are not limited to, rotator cuff repairs/procedures, slap lesion repairs/procedures, labral/repair procedures, or in connection with other known suture management techniques for the shoulder, knee, hip, and other joint procedures, as well as other procedures of manipulating soft tissue.

The description of the present teachings is merely exemplary in nature and, thus, variations that do not depart from the gist of the present teachings are intended to be within the scope of the present teachings. Such variations are not to be regarded as a departure from the spirit and scope of the present teachings.

What is claimed is:

1. A suture pushing device to push a suture through tissue, comprising:

a handle;

a shaft extending from the handle;

a suturing head at the distal end of the shaft, the suturing head comprising:

a first jaw;

a second jaw coupled to the first jaw; and a cutting edge formed on at least one of the first jaw or the second jaw to cut an opening into and through the tissue; and a blunt suture pushing member adapted to pass through the cut opening in the tissue and to push the suture through the cut opening in the tissue.

2. The suture pushing device according to claim 1, further comprising a suture pushing member receptacle to receive the blunt suture pushing member.

3. The suture pushing device according to claim 2, further comprising a retention mechanism to maintain the suture at the suturing head.

4. The suture pushing device according to claim 1, wherein the blunt suture pushing member contains a plurality of roughened surface features on the distal end of the suture pushing member to push the suture through the opening in the tissue cut by the cutting edge formed on the at least one of the first jaw or the second jaw.

5. The suture pushing device according to claim 4, wherein the roughened surface features are non-piercing.

6. The suture pushing device according to claim 1, wherein the blunt suture pushing member is made of a flexible material and has a distal end that is blunt, and wherein the distal end of the blunt suture pushing member engages the suture to carry the suture through the opening in the tissue.

7. The suture pushing device according to claim 6, wherein the flexible material comprises Nitinol.

8. The suture pushing device according to claim 1, wherein the handle comprises a trigger and a hammer.

9. The suture pushing device according to claim 8, wherein the trigger is actuable to move at least one of the second jaw or the first jaw with respect to the other jaw.

10. The suture pushing device according to claim 9, wherein the hammer is actuable to advance the blunt suture pushing member through the cut opening in the tissue.

11. The suture pushing device according to claim 1, wherein the second jaw includes a ramp for the blunt suture pushing member.

12. The suture pushing device according to claim 11, further comprising a suture pushing member receptacle, wherein the ramp is in communication with the suture pushing receptacle to guide the suture.

13. The suture pushing device according to claim 12, wherein the suture pushing member receptacle includes a suture retaining mechanism adapted to hold the suture in the first jaw.

14. The suture pushing device according to claim 1, further comprising a suture delivery channel adapted to arrange the suture for contact with the suture pushing member.

15. The suture pushing device according to claim 1, wherein the cutting edge is formed on both a distal end of the first jaw and a distal end of the second jaw, the cutting edge is configured to pierce through the tissue, and the cutting edge has a tooth shape.

16. A suture pushing device to push a suture through tissue, comprising:

a handle including a trigger and a hammer;

a shaft extending from the handle;

a suturing head at the distal end of the shaft, the suturing head comprising:

a first jaw;

a second jaw coupled to the first jaw and including a ramp; and a cutting edge formed on at least one of the first jaw or the second jaw to cut an opening into and through the tissue; and a blunt suture pushing member adapted to pass through the cut opening in the tissue and to push the suture through the cut opening in the tissue, wherein the trigger is actuable to move at least one of the second jaw or the first jaw with respect to the other jaw and wherein the hammer is actuable to advance the blunt suture pushing member through the cut opening in the tissue.

17. The suture pushing device according to claim 16, further comprising a suture pushing member receptacle in communication with the ramp of the second jaw to receive the suture and including a suture retaining mechanism.

18. The suture pushing device according to claim 17, wherein the suture retaining mechanism is selected from one of a flexible flap and a flexible block that bias the suture within the suture pushing member receptacle to retain the suture.

19. A suture pushing device to push a suture through tissue, comprising:

a handle including a trigger and a hammer;

a shaft extending from the handle;

a suturing head at the distal end of the shaft, the suturing head comprising:

a first jaw;

a second jaw coupled to the first jaw; and a cutting edge formed on and extending from at least one of the first jaw or the second jaw to cut an opening into and through the tissue; and a blunt suture pushing member adapted to pass through the cut opening in the tissue and to push the suture through the cut opening in the tissue, with the distal end of the blunt suture pushing member containing a plurality of roughened surface features to push the suture, wherein the trigger is actuable to move at least one of the second jaw or the first jaw with respect to the other jaw, and wherein the hammer is actuable to advance the blunt suture pushing member through the cut opening in the tissue.

20. The suture pushing device according to claim 19, further comprising a suture pushing member receptacle, wherein the second jaw includes a ramp that is in communication with the suture pushing member receptacle to guide the suture through the suture pushing member receptacle and the cut opening in the tissue.

* * * * *